United States Patent [19]
Feldmann-Krane et al.

[11] Patent Number: 5,401,871
[45] Date of Patent: Mar. 28, 1995

[54] ORGANOPOLYSILOXANE POLYETHERS AND THEIR USE AS HYDROLYSIS-RESISTANT WETTING AGENTS IN AQUEOUS SYSTEMS

[75] Inventors: Georg Feldmann-Krane, Mülheim; Werner Höhner, Velbert; Dietmar Schaefer, Hattingen; Stefan Silber, Krefeld, all of Germany

[73] Assignee: Th. Goldschmidt AG, Essen, Germany

[21] Appl. No.: 202,399

[22] Filed: Feb. 24, 1994

[30] Foreign Application Priority Data

Feb. 25, 1993 [DE] Germany .......................... 43 05 794.2
May 27, 1993 [DE] Germany .......................... 43 17 605.4

[51] Int. Cl.$^6$ ................................................. C07F 7/08
[52] U.S. Cl. .................................... 556/445; 556/437; 252/351; 504/116
[58] Field of Search ................ 556/445, 437; 504/116; 252/351; 514/772

[56] References Cited

U.S. PATENT DOCUMENTS

| | | |
|---|---|---|
| 3,299,112 | 1/1967 | Bailey . |
| 5,104,998 | 4/1992 | Ichinohe .............................. 556/445 |
| 5,145,879 | 9/1992 | Budnik et al. .................. 556/445 X |
| 5,260,469 | 11/1993 | Swiatek .................... 556/445 |
| 5,288,831 | 2/1994 | Ichinohe et al. ................ 556/445 X |
| 5,306,737 | 4/1994 | Burkhart et al. ............... 556/445 X |

Primary Examiner—Paul F. Shaver
Attorney, Agent, or Firm—Anderson Kill Olick & Oshinsky

[57] ABSTRACT

Organopolysiloxane polyethers with increased resistance to hydrolysis are prepared. Furthermore, a method of rendering an aqueous system hydrolysis-resistant and exhibiting increased wetting property utilizing such polysiloxane polyethers as wetting agents in aqueous systems is described. Aqueous coating systems containing such polyethers exhibit increased wetting property and are resistant to alkaline and acidic hydrolysis.

10 Claims, No Drawings

ORGANOPOLYSILOXANE POLYETHERS AND THEIR USE AS HYDROLYSIS-RESISTANT WETTING AGENTS IN AQUEOUS SYSTEMS

FIELD OF INVENTION

The invention relates to organopolysiloxane polyethers with increased resistance to hydrolysis. The invention furthermore relates to a method of rendering an aqueous coating system hydrolysis-resistant and imparting the system with an increased wetting property by adding such polysiloxane polyethers as wetting agents in aqueous systems. The invention also relates to aqueous systems used for coating containing such polyethers.

BACKGROUND INFORMATION AND PRIOR ART

Organopolysiloxane polyethers have long been known. They generally consist of an organopolysiloxane having polyoxyalkylene blocks linked terminally and/or laterally. The polyoxyalkylene blocks can be linked to the polysiloxane over SiC or SiOC bonds.

U.S. Pat. No. 3,299,112 is named as being representative of the closest state of the art. This patent discloses a siloxane, which is composed exclusively of (a) a group of the formula

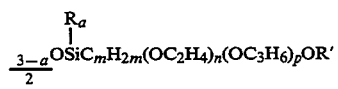

and (b) 1 to 4 groups of the formula

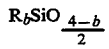

wherein the groups and subscripts have the following meanings:
a has a value of 0 to 2,
b has a value of 2 to 3,
R is a methyl or ethyl group,
$R^1$ is an alkyl group with 1 to 4 carbon atoms,
m has a value of 2 to 4,
n has an average value of 4 to 17,
p has an average value of 0 to 5
the ratio of n: p is at least 2:1,
the sum of n+p has a value of 4 to 17,
the polyoxyalkylene group is linked to the silicon atom of the (a) unit over at least 2 carbon atoms of the $C_mH_{2m}$ group.

It is shown in the aforementioned U.S. patent that these compounds can be used particularly as wetting agents in aqueous systems.

It has turned out, however, that compounds of this structure have only a limited hydrolysis resistance. Particularly in acidic or basic aqueous solutions, there is splitting of the SiOSi bond and the hydrolysis products can once again be subject to condensation, so that, in the course of the hydrolytic degradation, higher molecular weight organopolysiloxane polyethers, which have a decreased or no wetting action, are formed by a further condensation.

OBJECT OF THE INVENTION

An object of the present invention is organopolysiloxane polyethers having improved resistance to hydrolysis, thus retaining their wetting action over a longer period of time. This retention of wetting action is necessary particularly when aqueous preparations which contain these wetting agents are to be kept for a period of several months before they are used. This is the case, for example, with aqueous coating systems which are produced by the manufacturer and, after they are delivered to the dealer, kept by the latter for several months before they are used as intended. Accordingly, an effort is made to find organopolysiloxane polyethers which are resistant to hydrolysis in aqueous systems for at least several months and, if possible, one to two years.

Another object of the present invention is a method of rendering an aqueous coating system hydrolysis-resistant and exhibiting an increased wetting property utilizing the inventive polyethers. Yet another object of the present invention is an aqueous coating system comprising the inventive polyethers.

SUMMARY OF THE INVENTION

Surprisingly, it was discovered that these properties are to be found in organopolysiloxane polyethers of the general formula

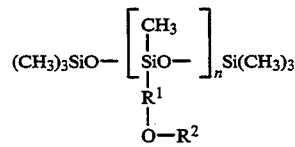

wherein
$R^1$ is a divalent, optionally branched alkylene group with 3 to 6 carbon atoms in the alkylene chain,
$R^2$ is a group of the formula $(C_mH_{2m}O-)_sR^3$, in which
m is a number greater than 2.0 and not greater than 2.5,
s is a number from 4 to 21
and $R^3$ is a hydrogen group, an alkyl group with 1 to 4 carbon atoms or an acetyl group, on the condition that, when the $R^1$ group has only 3 to 4 carbon atoms, a blockwise arrangement of the oxyalkylene units corresponding to the formula $(C_3H_6O-)_p(C_2H_4O-)_q(C_3H_6O-)_1R^3$ must be maintained, in which
p is a number from 1 to 3,
q is a number from 4 to 15 and
r is a number from 0 to 3,
n is a number from 1 to 3,
with the proviso that at least 50 mole percent of the oxyalkylene groups are oxyethylene groups.

$R^1$ is a divalent, optionally branched alkylene group with 3 to 6 carbon atoms in the alkylene chain. Examples of such groups are

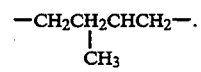

Especially preferred are the —(CH$_2$)$_3$— and the —(CH$_2$)$_6$— groups.

$R^2$ can have two different meanings, which depend on the number of carbon atoms in the $R^1$ group: $R^2$ generally represents the $(C_mH_{2m}O-)_s$ group, wherein m is a number greater than 2.0 and not greater than 2.5 and s is a number from 4 to 21. The subscript m arises out of the ratio of oxyethylene to oxypropylene units in the polyether and can assume any value greater than 2.0 and not greater than 2.5. If m has a value of 2.5, then this means for the case in which, aside from oxyethylene units, only oxypropylene units are present, that 50 mole percent of the oxyalkylene units are oxyethylene units and 50 mole percent of the oxyalkylene units are oxypropylene units. The total number of oxyalkylene units is given by the value of the subscript s.

The oxyalkylene units can be arranged in random or block order. However, if the number of carbon atoms in the $R^1$ group is equal to 3 or 4, only the blockwise arrangement of the oxyalkylene groups is permissible, so that the $R^2$ must then correspond to the $(C_3H_6O-)_p(C_2H_4O-)_q(C_3H_6O-)_rR^3$, wherein p is a number from 1 to 3, q is a number from 4 to 15 and r is a number from 0 to 3. The subscripts p, q and r are average values. If the $R^1$ group has 3 or 4 carbon atoms, the polyoxyalkylene chain of the $R^2$ group commences with at least one oxypropylene unit. By these means, it is ensured that the inventive compounds have the desired resistance to hydrolysis even when the number of carbon atoms of the $R^1$ group is low.

n indicates the number of difunctional siloxy units and has a value from 1 to 3.

In order to ensure the water solubility and wetting properties of the organopolysiloxane polyether, the condition must be met that at least 50 mole percent of the oxyalkylene groups are oxyethylene groups.

Preferably, the $-R^1-O-R^2$ group has a molecular weight of 400 to 700.

$R^3$ is a hydrogen group, an alkyl group with 1 to 4 carbon atoms or an acetyl group. Preferably, $R^3$ is a hydrogen group.

Examples of the inventive compounds are

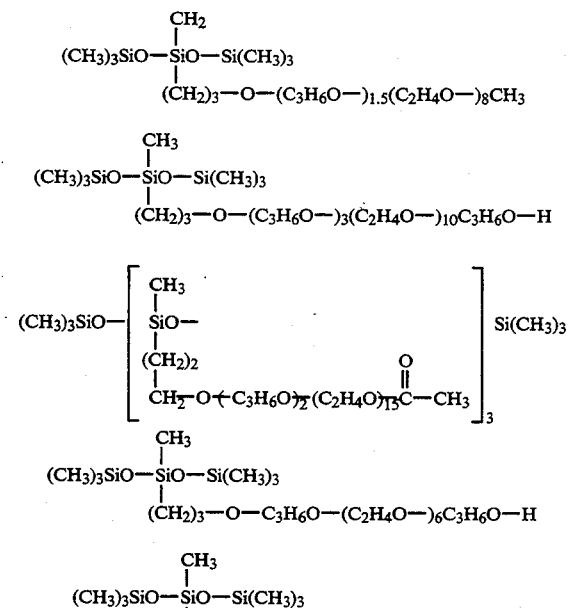

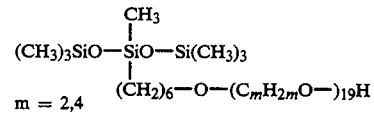

The inventive compounds are synthesized in the well-known way by the addition reaction between a polyether, the starting alcohol of which has a terminal, olefinic double bond, and a hydrogensiloxane in the presence of platinum catalysts.

The inventive compounds have the desired resistance to hydrolysis and have outstanding wetting properties. They are therefore particularly suitable as wetting agents in aqueous coating systems, as well as in aqueous preparations of agricultural chemicals, such as herbicides, pesticides and fungicides. The compounds are added to the aqueous preparations in amounts of 0.01 to 1% by weight. Higher amounts generally need not be added.

In the following Examples, the known synthesis of the inventive compounds is shown, it being understood that the Examples are given by way of illustration and not by way of limitation. The wetting action of the aqueous preparations, which contain the inventive compounds, is indicated by means of spreading measurements. The long-term resistance to hydrolysis is demonstrated in short-term tests by the improved stability of the compounds in acidic and alkaline solutions kept at 50° C. and compared with the resistance to hydrolysis of products of the state of the art.

EXAMPLE 1a

Synthesis of an Organopolysiloxane Polyether of the Average Formula

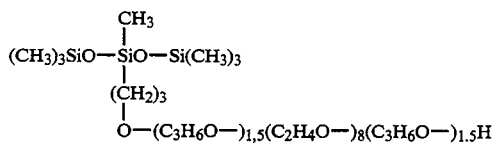

A polyether (700 g, 1.2 moles) starting from allyl alcohol and having the average formula $$CH_2=CH-CH_2O-(C_3H_6O-)_{1.5}(C_2H_4O-)_8(C_3H_6O-)_{1.5}H$$

is mixed with 30 mg (0.07 mmoles) of hexachloroplatinic acid and heated to 110° C. Over a period of one hour, 222 g (1 mole) of 1,1,1,3,5,5,5-heptamethyltrisiloxane is added dropwise and the reaction mixture is stirred for a further 4 hours at this temperature. After this period, more than 90% of the SiH groups have been converted. The resulting organopolysiloxane polyether has a viscosity of about 100 mPas at 25° C.

EXAMPLE 1b

Synthesis of an Organopolysiloxane Polyether Having the Average Formula

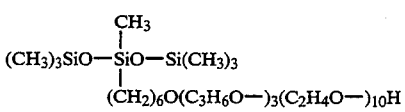

A polyether (857 g, 1.2 moles), starting from 5-hexen-1-ol and having the average formula $$CH_2=CH-(CH_2-)_4O(C_3H_6O-)_3(C_2H_4O-)_{10}H$$

is mixed with 30 mg (0.07 mmoles) of hexachloroplatinic acid and heated to 105° C. Over a period of one hour, 222 g (1.0 mole) of 1,1,1,3,5,5,5-heptamethyltrisiloxane is added dropwise and the reaction mixture is stirred for a further 4 hours at this temperature. After this period, more than 90% of the SiH groups have been converted. The resulting organopolysiloxane polyether has a viscosity of about 100 mPas at 25° C.

EXAMPLE 2

Comparison of the Wetting Action and Resistance to Hydrolysis of Aqueous Solutions of Organopolysiloxane Polyethers Synthesized According to Examples 1a and 1b Under Acidic (pH 5) and Alkaline (pH 9) Conditions In Comparison with Products of the State of the Art Product 1: inventive compound of Example 1a
Product 2: inventive compound of Example 1b
Product 3: not of the invention; average formula:

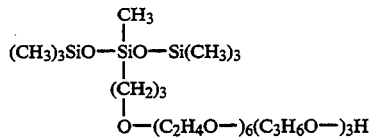

Product 4: not of the invention; average formula

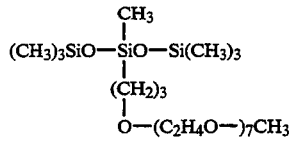

A: Wetting Action Under Acidic Conditions (pH 5)

Organopolysiloxane polyethers (0.1 g) are dissolved in 100 mL of distilled water, the pH of which had previously been adjusted to a value of 5.0 by means of potassium hydrogen phthalate buffer. This solution (0.05 mL) is applied by means of a micropipette on a PVC sheet. As a result of the low surface tension of the aqueous organopolysiloxane polyether solution, the water droplet applied spreads spontaneously on the PVC sheet. The diameter of the wetted area (measured in mm), occupied by the aqueous solution, is a direct measure of the wetting action of the organopolysiloxane. To check the resistance to hydrolysis of the organopolysiloxane polyether in aqueous solution at a pH of 5, wetting tests are carried out immediately after the solution is prepared, as well as 24 hours, 72 hours, 1 week, 2 weeks and 3 weeks afterwards. For the duration of the experiment, the aqueous solutions are kept at 50° C. The hydrolytic decomposition is indicated by the decreasing spreading action. The results are summarized in Table 1.

TABLE 1

Spreading of Aqueous Organopolysiloxane Polyether Solutions (Kept at 50° C.) (0.05 mL; 0.1%) at a pH of 5.0 on PVC Sheets

| Product | Starting Value | 24 Hours | 72 Hours | 1 Week | 2 Weeks | 3 Weeks |
|---|---|---|---|---|---|---|
| Without Surfactant | 8 | 8 | 8 | 8 | 8 | 8 |
| Product 1 | 40 | 40 | 40 | 38 | 33 | 27 |
| Product 2 | 40 | 40 | 40 | 40 | 40 | 36 |
| Product 3 | 44 | 32 | 15* | 8 | 8 | 8 |
| Product 4 | 42 | 30 | 23 | 14* | 8 | 8 |

*Failure to wet

B: Wetting Action Under Alkaline Conditions (pH 9)

Organopolysiloxane polyethers (0.2 g) are dissolved in 100 mL of distilled water, the pH of which had been previously adjusted to a value of 9.0 by means of sodium borate buffer. The solution is applied on the PVC sheet and the wetting action as well as the resistance to hydrolysis are evaluated as described under A. The results are summarized in Table 2.

TABLE 2

Spreading of Aqueous Organopolysiloxane Polyether Solutions (Kept at 50° C.) (0.05 mL; 0.2%) at a pH of 9 on PVC Sheet

| Product | Starting Value | 24 Hours | 72 Hours | 1 Week | 2 Weeks | 3 Weeks |
|---|---|---|---|---|---|---|
| Without Surfactant | 8 | 8 | 8 | 8 | 8 | 8 |
| Product 1 | 40 | 40 | 40 | 40 | 38 | 34 |
| Product 2 | 40 | 40 | 40 | 37 | 33 | 28 |
| Product 3 | 44 | 22* | 15* | 8 | 8 | 8 |
| Product 4 | 42 | 36 | 26 | 17* | 8 | 8 |

*Failure to wet

The superiority of the inventive organopolysiloxane polyether with respect to its hydrolytic stability is clearly evident from the results shown.

We claim:

1. An Organopolysiloxane polyether of the general formula

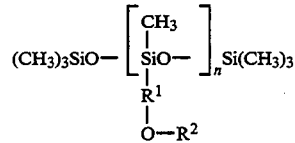

wherein
$R^1$ is a divalent, optionally branched alkylene group with 3 to carbon atoms in the alkylene chain,
$R^2$ is a group of the formula $(C_mH_{2m}O-)_sR^3$, in which m is a number greater than 2.0 and not greater than 2.5, s is a number from 4 to 21 and $R^3$ is a hydrogen group, an alkyl group with 1 to 4 carbon atoms or an acetyl group, on the condition that, when Rgroup has only 3 to 4 carbon atoms, a blockwise arrangement of the oxyalkylene units corresponding to the formula $(C_3H_6O-)_p(C_2H_4O-)_q(C_3H_6O-)_1R^3$ must be maintained, in which p is a number from 1 to 3, q is a number from 4 to 15 and r is a number from 0 to 3,
n is a number from 1 to 3,
with the proviso that at least 50 mole percent of the oxyalkylene groups are oxyethylene groups.

2. The organopolysiloxane polyether of claim 1, further comprising that $R^1$ is a $-(CH_2)_a$ group, wherein a is a number from 3 to 6.

3. The organopolysiloxane polyether of claim 1, comprising that $R^3$ is a hydrogen group.

4. The organopolysiloxane polyether of claim 1, further comprising that n is equal to 1.

5. The organopolysiloxane polyether of claim 1, further comprising that p is equal to 1 to 1.5.

6. The organopolysiloxane polyether of claim 1, further comprising that q is equal to 5 to 10.

7. The organopolysiloxane polyether of claim 1, further comprising that r is equal to 1 to 1.5.

8. The organopolysiloxane polyether of claim 1, comprising that the molecular weight of the $-R^1-O-R^2$ group is 400 to 700.

9. An aqueous preparation used for coating systems comprising about between 0.01 and 1% by weight, based on the preparation, of the organopolysiloxane polyether of claim 1.

10. A method of rendering an aqueous coating system hydrolysis-resistant and imparting the system with an increased wetting property comprising the steps of adding to the system about between 0.01 and 1% by weight, based on the system, of the organopolysiloxane polyether of claim 1.

* * * * *